United States Patent
Golz-Berner et al.

(10) Patent No.: US 7,361,372 B2
(45) Date of Patent: Apr. 22, 2008

(54) ACTIVE PREPARATION CONTAINING PLANT EXTRACTS FOR COSMETICS

(75) Inventors: Karin Golz-Berner, Monaco (MC); Leonhard Zastrow, Monaco (MC)

(73) Assignee: Coty B.V., Haarlem (NL)

( * ) Notice: Subject to any disclaimer, the term of this patent is extended or adjusted under 35 U.S.C. 154(b) by 365 days.

(21) Appl. No.: 10/558,441

(22) PCT Filed: May 21, 2004

(86) PCT No.: PCT/EP2004/005542

§ 371 (c)(1),
(2), (4) Date: Nov. 28, 2005

(87) PCT Pub. No.: WO2004/105706

PCT Pub. Date: Dec. 9, 2004

(65) Prior Publication Data

US 2006/0251607 A1    Nov. 9, 2006

(30) Foreign Application Priority Data

May 28, 2003    (DE) ................. 103 25 156

(51) Int. Cl.
*A01N 65/00* (2006.01)
*A61K 36/82* (2006.01)
*A61K 36/48* (2006.01)
*A61K 36/232* (2006.01)

(52) U.S. Cl. .............. 424/729; 424/757; 424/776; 424/774; 424/773; 426/45

(58) Field of Classification Search ............ None
See application file for complete search history.

(56) References Cited

FOREIGN PATENT DOCUMENTS

| WO | WO 99/66881 | 12/1999 |
|---|---|---|
| WO | WO 01/26617 | 4/2001 |

OTHER PUBLICATIONS http://en.wikipedia.org/wiki/Camellia_sinensis. "*Camellia sinensis*". Downloaded Jan. 17, 2008.*
http://en.wikipedia.org/wiki/Pongamia_pinnata. "*Pongamia pinnata*". Downloaded Jan. 17, 2008.*
http://www.hort.purdue.edu/newcrop/duke_energy/Pongamia_pinnata.html. "*Pongamia pinnata* (L.) Pierre". Downloaded Jan. 17, 2008.*
http://en.wikipedia.org/wiki/Garden_angelia. "*Garden Angelica*". Downloaded Jan. 17, 2008.*
http://www.botanical.com/botanical/mgmh/a/anegl037.html. "*Angelica*". Downloaded Jan. 17, 2008.*
http://en.wikipedia.org/wiki/Coffea. "*Coffea*". Downloaded Jan. 17, 2008.*

* cited by examiner

*Primary Examiner*—Michele Flood
(74) *Attorney, Agent, or Firm*—Akerman Senterfitt; Stephen A. Pendorf; Gregory M. Lefkowitz

(57) ABSTRACT

The invention relates to an active ingredient composition used in cosmetic products, said composition containing vegetable extracts and combating in particular free radicals. The active ingredient composition is an alcohol-based mixture of vegetable extracts that is devoid of liposomes, consisting of between 0.1 and 2 wt. % green coffee-bean extract, between 0.1 and 2 wt. % *Camellia sinensis* leaf extract, between 0.1 and 2 wt % *Pongamia pinnata* extract and between 0.1 and 2 wt. % *Angelica archangelica* root extract and a residual content of a monovalent C2-C5 alcohol to obtain the total of 100 wt. %. The free radical protection factor amounts to $1400\text{-}2900 \times 10^{14}$ free radicals per mg.

4 Claims, No Drawings

ACTIVE PREPARATION CONTAINING PLANT EXTRACTS FOR COSMETICS

CROSS REFERENCE TO RELATED APPLICATION

This application is a national stage of PCT/EP2004/005542 filed May 21, 2004 and based upon DE 103 25 156.1 filed May 28, 2003 under the International Convention.

BACKGROUND OF THE INVENTION

1. Field of the Invention

The invention relates to an active preparation for cosmetics, which contains plant extracts and has special anti-radical properties.

2. Related Art of the Invention

From WO 99/66881, a cosmetic active preparation with a high radical protection factor is known, which contains an extract from the bark of Quebracho blanco enclosed in microcapsules and a silkworm extract as main ingredients, which extracts are provided in a gel together with phospholipids and form an association complex in said gel. The aforesaid active complex can in addition contain further ingredients, e.g. plant extracts. Plant extracts mentioned include, among many others, those obtained from coffee beans and angelica root. Said combinations have radical protection factors ranging between 100 and 10,000, and the cosmetic preparations in which they are used have radical protection factors of 40-200, depending on the amount of the active preparation added.

SUMMARY OF THE INVENTION

The object of the invention is to provide a composition for use in cosmetics, which can be easily prepared without using encapsulating liposomes and which at the same time has a high radical protection factor, but can be combined much more easily with other cosmetic ingredients and is also suitable for the production of perfumes and sprays.

According to the invention, the active preparation consists of a mixture of plant extracts with an alcoholic base, which consists of 0.1 to 2% by weight extract from green coffee beans, 0.1 to 2% by weight extract from the leaves of *Camellia sinensis*, 0.1 to 2% by weight extract from *Pongamia pinnata* and 0.1 to 2% by weight extract from the roots of *Angelica archangelica*, a monovalent $C_2$-$C_5$ alcohol making up the remainder up to 100% by weight. The extract mixture is free from liposomes and has a radical protection factor ranging between 1,400 and $2,900 \times 10^{14}$ radicals per mg.

The aforesaid extracts are alcoholic or aqueous-alcoholic extracts, preferably alcoholic extracts. The extraction temperatures range between 18 and 28° C. The extract from *Pongamia pinnata* was obtained from the whole plant.

The extract mixture can make up 0.1 to 10% by weight, preferably 0.1 to 5% by weight, of a cosmetic, relative to the cosmetic's total weight. It has been found that such an active mixture has an unexpectedly high radical protection factor (RPF) of approx. $1,400$-$2,900 \times 10^{14}$ radicals per mg, determined by measuring the number of free radicals in a solution of a test substance ($S_1$) by means of electron spin resonance (ESR) and comparing it with the ESR measuring result of the cosmetic active preparation according to the equation $$RPF = (RC \times RF)/PI$$

wherein $RF = (S_1 - S_2)/S_1$; RC=concentration of the test substance (radicals/ml); PI=concentration of the active preparation (mg/ml) (measurement according to WO 99/66881).

The RPF found in this way is considerably higher than that of an active preparation in WO 99/66881, which is specified to be 1,255.

It has further been found that a cosmetic composition containing the active preparation according to the invention will have radical protection factors of 60 to $140 \times 10^{14}$ radicals per mg if said active preparation is contained in said cosmetic composition in a preferred concentration ranging between 0.5 and 2% by weight, which is considerably higher than the values of 35 to $49 \times 10^{14}$ specified in the examples of WO 99/66881.

The active preparation according to the invention can be used in W/O or O/W emulsions, gels or gel emulsions. Its use in perfumes or sprays is particularly advantageous. The active preparations known from WO 99/66881 are always combined with a gel and in addition the active agents are encapsulated in liposomes, which frequently makes it very difficult to atomize such formulations; as a consequence, these formulations with high radical protection factors can hardly be used for such applications. In contrast, the alcoholic solution of the active preparation according to the invention can be prepared more easily since no liposomes must be produced, it has high radical protection factors and it can be incorporated into spray or perfume applications and atomized by the user without problems.

The active preparation according to the invention can also be combined with other cosmetic auxiliaries and active agents and processed to obtain forms suitable for application.

Such auxiliaries include water, preservatives, colourants, pigments having a colouring effect, thickeners, fragrances, alcohols, polyols, esters, electrolytes, gel-forming agents, polar and non-polar oils, polymers, copolymers, emulsifiers, stabilizers.

Cosmetic active agents include e.g. inorganic and organic sunscreens, further radical scavengers, moisturizers, vitamins, enzymes, further plant-based active agents, polymers, melanin, antioxidants, anti-inflammatory natural active agents.

DETAILED DESCRIPTION OF THE INVENTION

The invention will hereinafter be explained in more detail by means of examples. All quantities are in % by weight unless indicated otherwise.

EXAMPLE 1

Moisturizing Skin Balm

| Phase A | |
|---|---|
| Water | q.s. ad 100 |
| Glycerine | 2.0 |
| Butylene Glycol | 2.0 |
| Tetrasodium Ethylenediamine Tetraacetic Acid | 0.1 |
| Preservative | 0.4 |
| pH adjuster | 0.3 |
| Phase B | |
| Beheneth-25 | 3.3 |
| Cetearyl Alcohol | 2.7 |
| Dicapryl Carbonate | 8.5 |
| Shea Butter | 7.2 |
| Phenoxyethanol | 0.9 |
| Modified maize starch powder | 3.0 |
| Dimethicone | 1.4 |
| Simulgel ® NS | 3.5 |
| Phase C | |
| Colourants | 0.1 |
| Water of volcanic origin** | 1.0 |
| Peptide palmitoyl-gly-his-lys | 0.5 |
| Mixture of alcoholic extracts from plants* | 0.2 |
| *Crithmum maritimum* extract | 0.5 |

-continued

| | |
|---|---|
| Hydrolyzed soy protein | 1.0 |
| Benzophenone-4 (for colourants) | 0.4 |

*Consisting of 0.2% by weight seeds of coffee beans, 0.2% by weight *Camelli sinensis* leaves, 0.2% by weight *Pongamia pinnata*, 0.2% by weight *angelica* root and 99.2% by weight ethanol; RPF 2630 × $10^{14}$ rad/mg.
**With the following salt concentrations:
0.01-0.05 mg/l Fe, 100-300 mg/l K, 1,000-2,000 mg/l Na, 80-200 mg/l Mg, 50-150 mg/l Ca, 50-150 mg/l Si (as $SiO_2$), 0.01-0.1 mg/l P, 0.001-0.005 mg/l Se, 0.01-0.03 mg/l Zn.

Phases A and B are mixed separately at approx. 60° C., Phase C is mixed at approx. 35° C., and all three phases are combined with one another while stirring at approx. 35° C.

The skin balm has an RPF of 68 (×$10^{14}$ radicals per mg).

EXAMPLE 2

Perfume

| | |
|---|---|
| Ethanol | q.s. ad 100 |
| Mixture of alcoholic extracts from plants* | 9.5 |
| Perfume | 8 |

RPF = 137.

EXAMPLE 3

Spray

| | |
|---|---|
| Ethanol | q.s. ad 100 |
| Mixture of alcoholic extracts from plants* | 5 |
| Propellant gas | 38 |

RPF = 93.

The spray was excellent to handle, showed a very fine droplet distribution and caused no such problems as comparative sprays in which plant extracts were encapsulated in liposomes.

The invention claimed is:

1. A cosmetic preparation with plant extracts comprising 0.1 and 10% by weight of an active preparation comprising a liposome-free mixture of plant extracts with an alcoholic base, which consists of 0.1 to 2% by weight extract from green coffee beans, 0.1 to 2% by weight extract from the leaves of *Camellia sinensis*, 0.1 to 2% by weight extract from *Pongamia pinnata* and 0.1 to 2% by weight extract from the roots of *Angelica archangelica*, and a monovalent $C_2$-$C_5$ alcohol making up the remainder up to 100% by weight, wherein the radical protection factor ranges between 1,400 and 2,900×$10^{14}$ radicals per milligram (mg) and wherein the aforesaid concentrations are relative to the total weight of the cosmetic preparation.

2. The cosmetic preparation according to claim 1, wherein said active preparation is a mixture of plant extracts with an alcoholic base, which consists of 0.2% by weight extract from green coffee beans, 0.2% by weight extract from the leaves of *Camellia sinensis*, 0.2% by weight extract from *Pongamia pinnata* and 0.2% by weight extract from the roots of *Angelica archangelica* and 99.2% by weight ethanol.

3. The cosmetic preparation according to claim 1, wherein said active preparation is provided in a cosmetic preparation in a concentration ranging between 0.1 and 10% by weight, and the radical protection factor of said cosmetic preparation ranges between 60 and 140×$10^{14}$ radicals per mg.

4. An active preparation according to claim 1, wherein said active preparation is provided in a spray or a perfume.

* * * * *